(12) United States Patent
Yang

(10) Patent No.: US 6,626,316 B2
(45) Date of Patent: Sep. 30, 2003

(54) TRASH CAN ASSEMBLY WITH TOE-KICK RECESS

(76) Inventor: Frank Yang, 4171 Pascal Pl., Palos Verdes Peninsula, CA (US) 90061

( * ) Notice: Subject to any disclaimer, the term of this patent is extended or adjusted under 35 U.S.C. 154(b) by 0 days.

(21) Appl. No.: 09/746,574

(22) Filed: Dec. 22, 2000

(65) Prior Publication Data

US 2002/0079315 A1 Jun. 27, 2002

(51) Int. Cl.[7] .............................................. B65D 43/26
(52) U.S. Cl. .................... 220/263; 220/908; 220/908.1; 220/908.2; 220/DIG. 13; 220/87.1; 239/274; 239/70
(58) Field of Search ................................ 220/610, 611, 220/612, 614, 908, 908.1, 908.2, 262, 263, 87.1, DIG. 13, 484, 636, 23, 87, 628, 638; 239/274, 67, 69, 70, 690, 692, 708; 361/230, 231; 49/263

(56) References Cited

U.S. PATENT DOCUMENTS

| | | | |
|---|---|---|---|
| 1,820,555 A * | 8/1931 | Buschman | 220/263 X |
| 1,891,651 A * | 12/1932 | Padelford et al. | 220/263 |
| 2,759,625 A * | 8/1956 | Ritter | 220/262 |
| 3,008,604 A * | 11/1961 | Garner | 220/263 X |
| 3,654,534 A * | 4/1972 | Fischer | 361/231 X |
| 4,081,105 A * | 3/1978 | Dagonnet et al. | 220/263 |
| 4,200,197 A * | 4/1980 | Meyer et al. | 220/263 |
| 4,913,308 A * | 4/1990 | Culbertson | 220/908.1 X |
| 4,918,568 A * | 4/1990 | Stone et al. | 361/231 |
| 4,972,966 A * | 11/1990 | Craft, Jr. | 220/264 |
| 5,065,272 A * | 11/1991 | Owen et al. | 361/231 |
| 5,147,055 A * | 9/1992 | Samson et al. | 220/263 X |
| 5,174,462 A * | 12/1992 | Hames | 220/908 |
| 5,226,558 A * | 7/1993 | Whitney et al. | 220/638 X |
| 5,230,525 A * | 7/1993 | Delmerico et al. | 220/263 X |
| 5,249,693 A * | 10/1993 | Gillispie et al. | 220/263 |
| 5,390,818 A * | 2/1995 | LaBuda | 141/390 |
| 5,474,201 A * | 12/1995 | Liu | 220/264 X |
| D377,554 S * | 1/1997 | Adriaansen | D34/7 |
| 6,010,024 A | 1/2000 | Wang | |
| D435,951 S * | 1/2001 | Yang et al. | 220/908 X |
| 6,364,147 B1 * | 4/2002 | Meinzinger et al. | 220/495.06 |

FOREIGN PATENT DOCUMENTS

| | | | | |
|---|---|---|---|---|
| DE | 19933180 | * | 1/2001 | |
| EP | 1 157 936 A2 | * | 11/2001 | |
| JP | 6-272888 | * | 9/1994 | 62/272 |
| WO | WO 92/02430 | * | 2/1992 | 220/263 |

* cited by examiner

*Primary Examiner*—Robin Hylton
(74) *Attorney, Agent, or Firm*—Raymond Sun (57) ABSTRACT

A trash can assembly has a shell having an enclosing wall that defines a periphery. The assembly has a lid fitted over the top of the shell, and a foot pedal positioned adjacent the bottom of the shell, with a portion of the foot pedal positioned inside the periphery of the shell. The assembly also includes a link assembly coupling the foot pedal and the lid. The assembly can also include a liner defining a container body, the liner fitted inside the shell and having an indent provided on the container body. A handle mechanism has a link strip that has a hooked end, with the hooked end engaging the indent to lift the liner from inside the shell.

15 Claims, 10 Drawing Sheets

TRASH CAN ASSEMBLY WITH TOE-KICK RECESS

BACKGROUND OF THE INVENTION

1. Field of the Invention

The present invention relates to household items, and in particular, to a trash can assembly that incorporates a number of improvements and enhancements.

2. Description of the Prior Art

A major concern for both the home and the workplace is containing and holding wastes, refuse, and trash until permanent disposal. Trash cans act as containers for holding trash and other wastes that are produced in any typical home or office. Trash and garbage cans often employ lids and covers to contain the trash and its associated odor, to hide the trash from view, and to prevent the trash from contaminating areas beyond the lid.

Conventional trash cans have been improved over the years to make them more user-friendly, sanitary, and hygienic. For example, many trash cans are now provided with a foot pedal positioned adjacent the base of the trash can so that a user can step on the foot pedal to open the lid of the trash can, thereby freeing up the user's hands to toss trash, or to change the plastic liner or bag that is used to line the trash can. Other trash cans have even provided an interior metal or plastic liner that fits inside the trash can, and which can be removed to be washed. However, these conventional trash cans still suffer from a number of drawbacks.

For example, the foot pedals on some of the conventional trash cans (e.g., such as shown in U.S. Pat. No. 6,010,024) are positioned awkwardly in that they extend a considerable distance from the body of the trash can to provide a sufficiently large surface area for the user's foot, and also to provide sufficient leverage for the user to step on and pivot the foot pedal. Unfortunately, such outwardly-extending foot pedals are prone to being inadvertently kicked by people as they walk around the vicinity of the trash can.

Other problems are associated with the internal liner. In conventional trash cans, the user typically needs to remove the liner from the trash can to dispose of the contents therein. To do so, the user typically lifts the liner from the trash can, and this may result in the user gripping portions of the interior of the liner, so that the user's fingers may come into contact with dirt, germs or trash items.

An additional problem relates to the fact that the wastes placed within such a container may produce odors, smells, and other harmful gases. Inevitably, the lid will need to be opened to deposit the waste, thereby allowing the odors and smells to escape from the trash can. Odors and smells may also escape from the trash can even when the lid is closed because some lids do not provide a tight seal with the trash can container.

Thus, there remains a need for a trash can that overcomes the drawbacks identified above.

SUMMARY OF THE DISCLOSURE

It is an object of the present invention to provide a trash can assembly that has an improved step pedal that is less prone to being kicked yet enhances its ability to control the opening of the lid of the trash can assembly.

It is another object of the present invention to provide a trash can assembly that allows the user to remove an internal liner in a sanitary manner.

It is another object of the present invention to provide a trash can assembly that minimizes the undesirable odor of the waste products stored therein.

In order to accomplish the objects of the present invention, there is provided a trash can assembly that has a shell having an enclosing wall that defines a periphery. According to one embodiment, the assembly has a lid fitted over the top of the shell, and a foot pedal positioned adjacent the bottom of the shell, with a portion of the foot pedal positioned inside the periphery of the shell. The assembly also includes a link assembly coupling the foot pedal and the lid.

According to another embodiment, the assembly has a liner defining a container body, the liner fitted inside the shell and having an indent provided on the container body. The assembly also includes a handle mechanism having a link strip that has a hooked end, with the hooked end engaging the indent to lift the liner from inside the shell.

According to yet another embodiment, the assembly has an air freshening device secured to its lid. The air freshening device can be a charcoal pad, or an electrical ionizer.

DETAILED DESCRIPTION OF THE PREFERRED EMBODIMENTS

The following detailed description is of the best presently contemplated modes of carrying out the invention. This description is not to be taken in a limiting sense, but is made merely for the purpose of illustrating general principles of embodiments of the invention. The scope of the invention is best defined by the appended claims. In certain instances, detailed descriptions of well-known devices and mechanisms are omitted so as to not obscure the description of the present invention with unnecessary detail.

Figure 1:
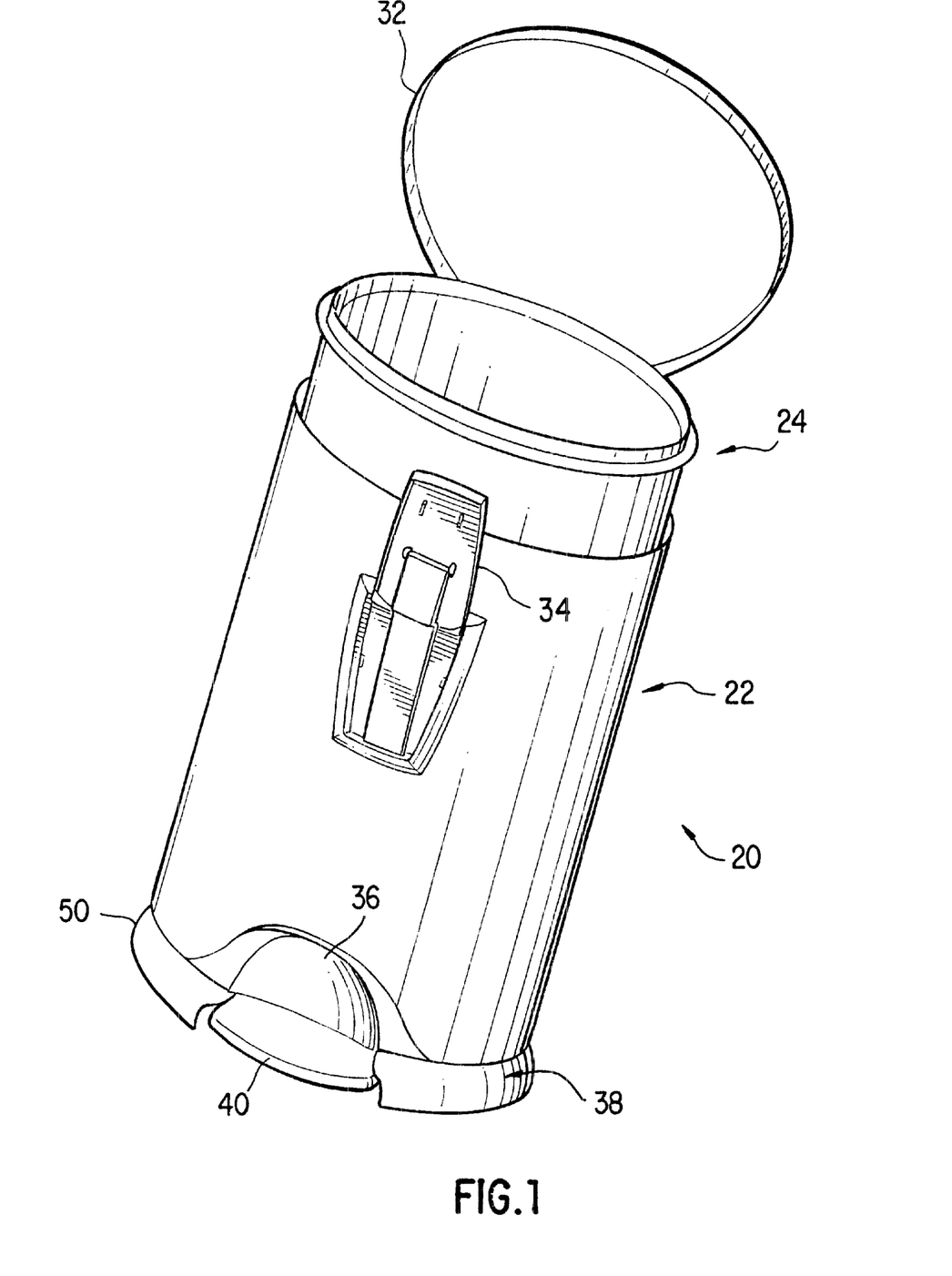
FIG. 1 is a front perspective view of the trash can assembly according to one embodiment of the present invention.
Figure 2:
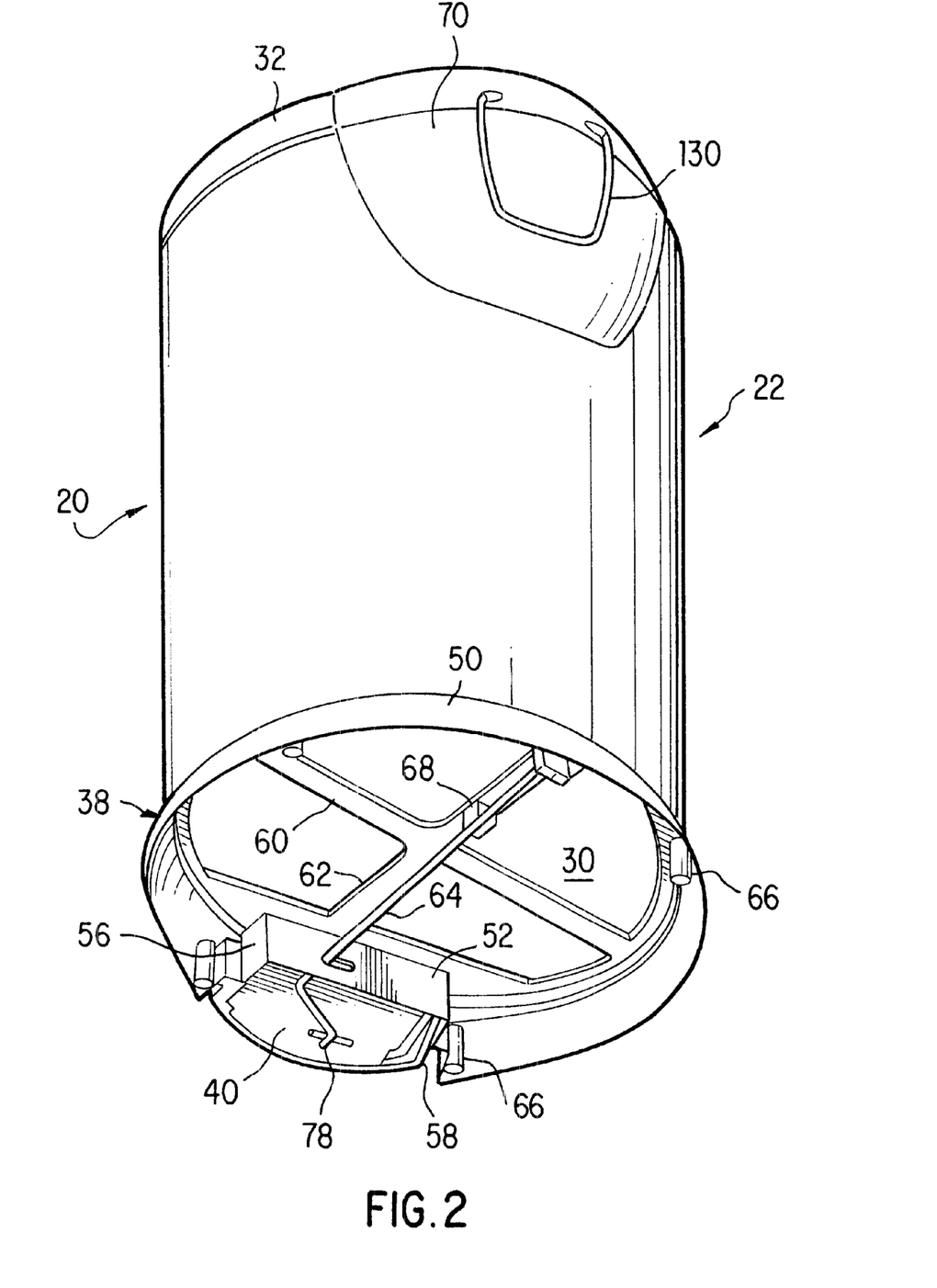
FIG. 2 is a bottom perspective view of the trash can assembly of FIG. 1.
Figure 3:
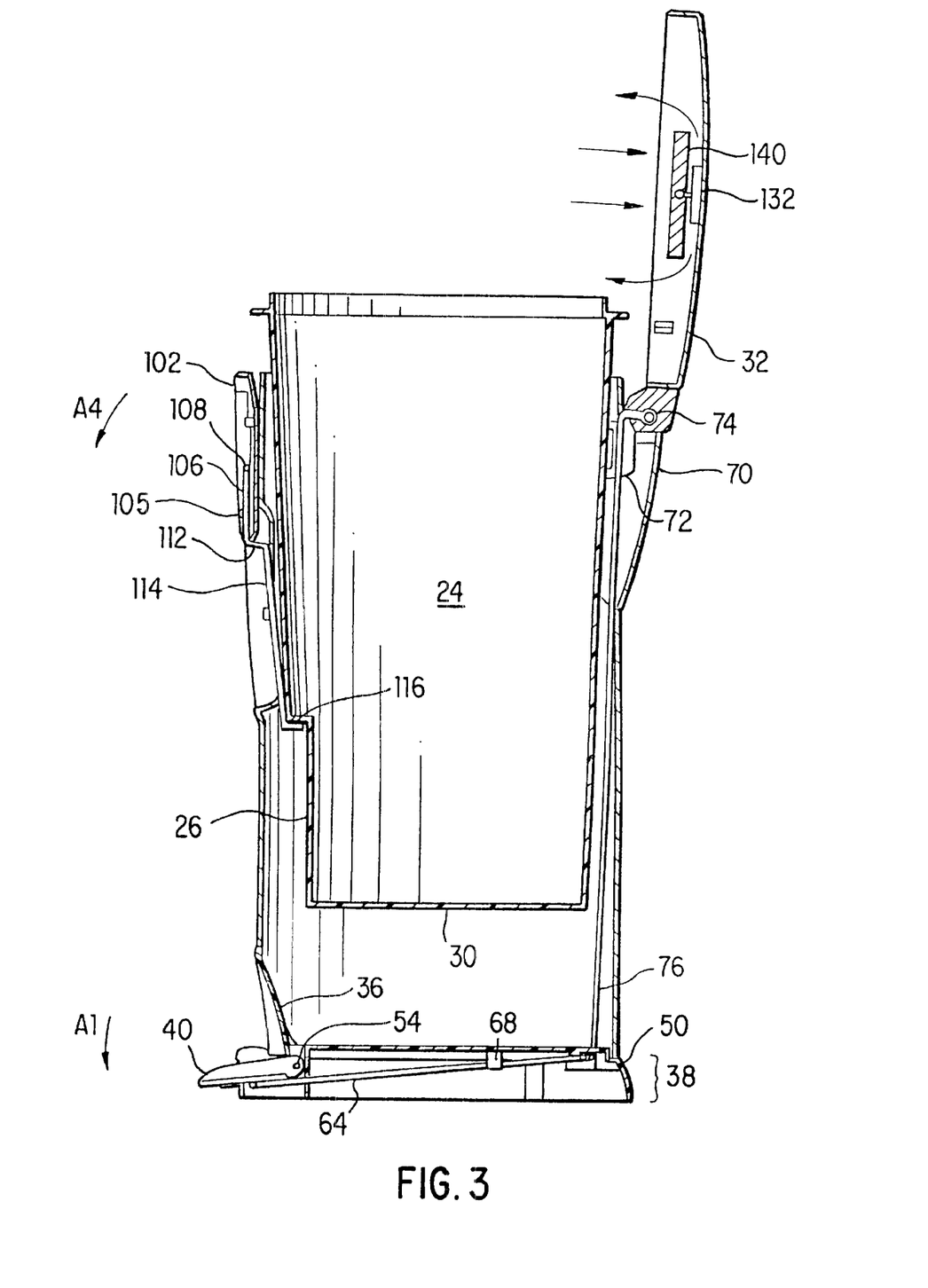
FIG. 3 is a cross-sectional side view of the trash can assembly of FIG. 1.
Figure 4:
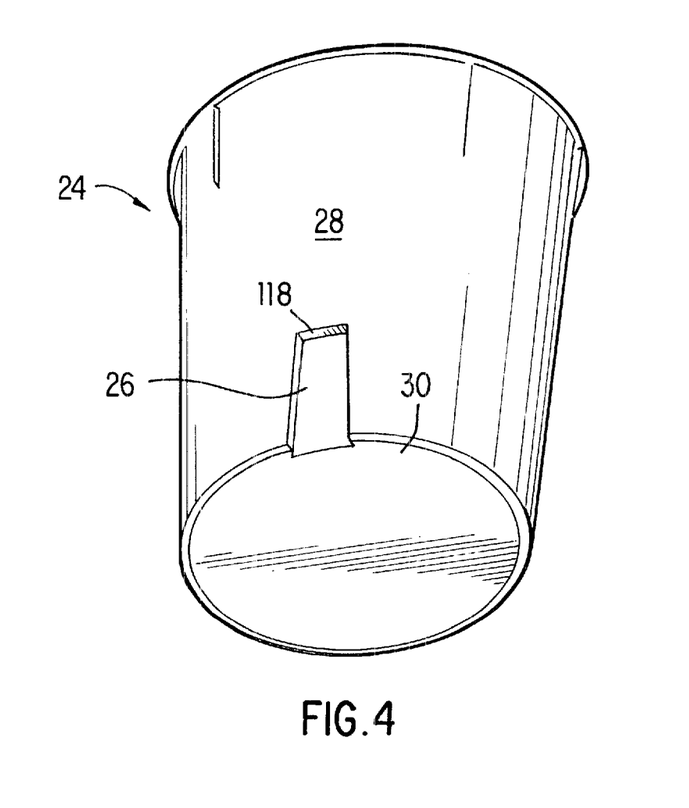
FIG. 4 is a bottom perspective view of a liner that can be used with the trash can assembly of FIG. 1.
Figure 5:
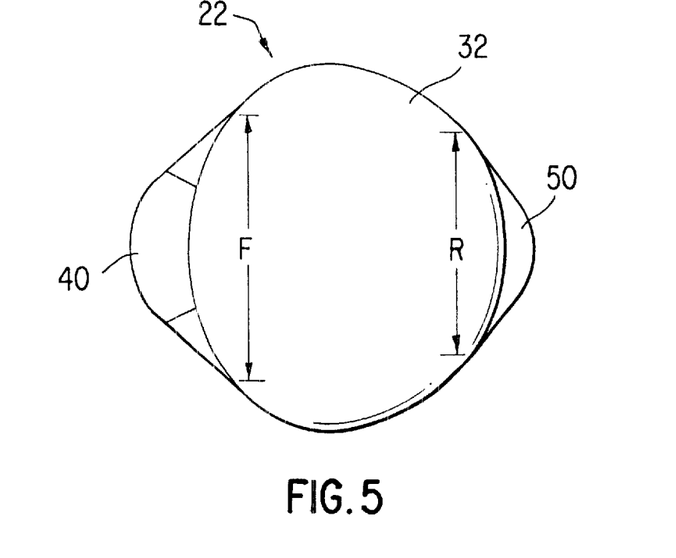
FIG. 5 is a top plan view of the trash can assembly of FIG. 1.
Figure 6A:
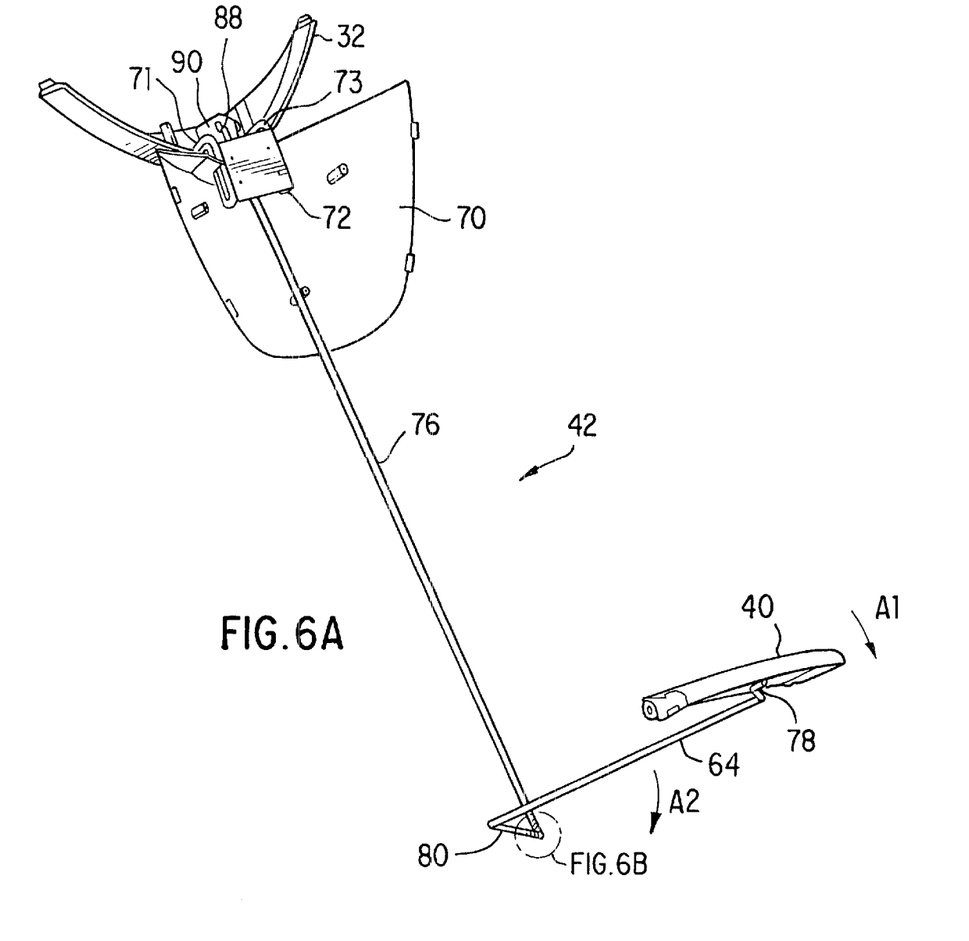
FIG. 6A is an isolated perspective view of a link assembly that can be used with the trash can assembly of FIG. 1.
Figure 6B:
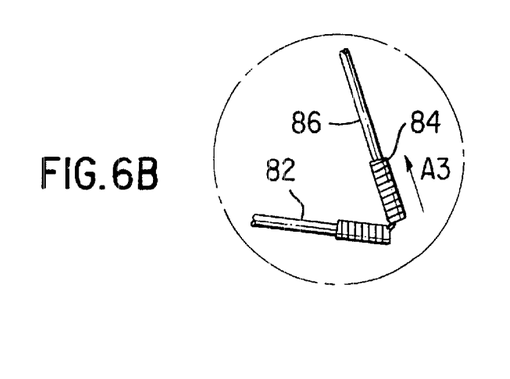
FIG. 6B illustrates the portion B of the link assembly of FIG. 6A.
Figure 6C:
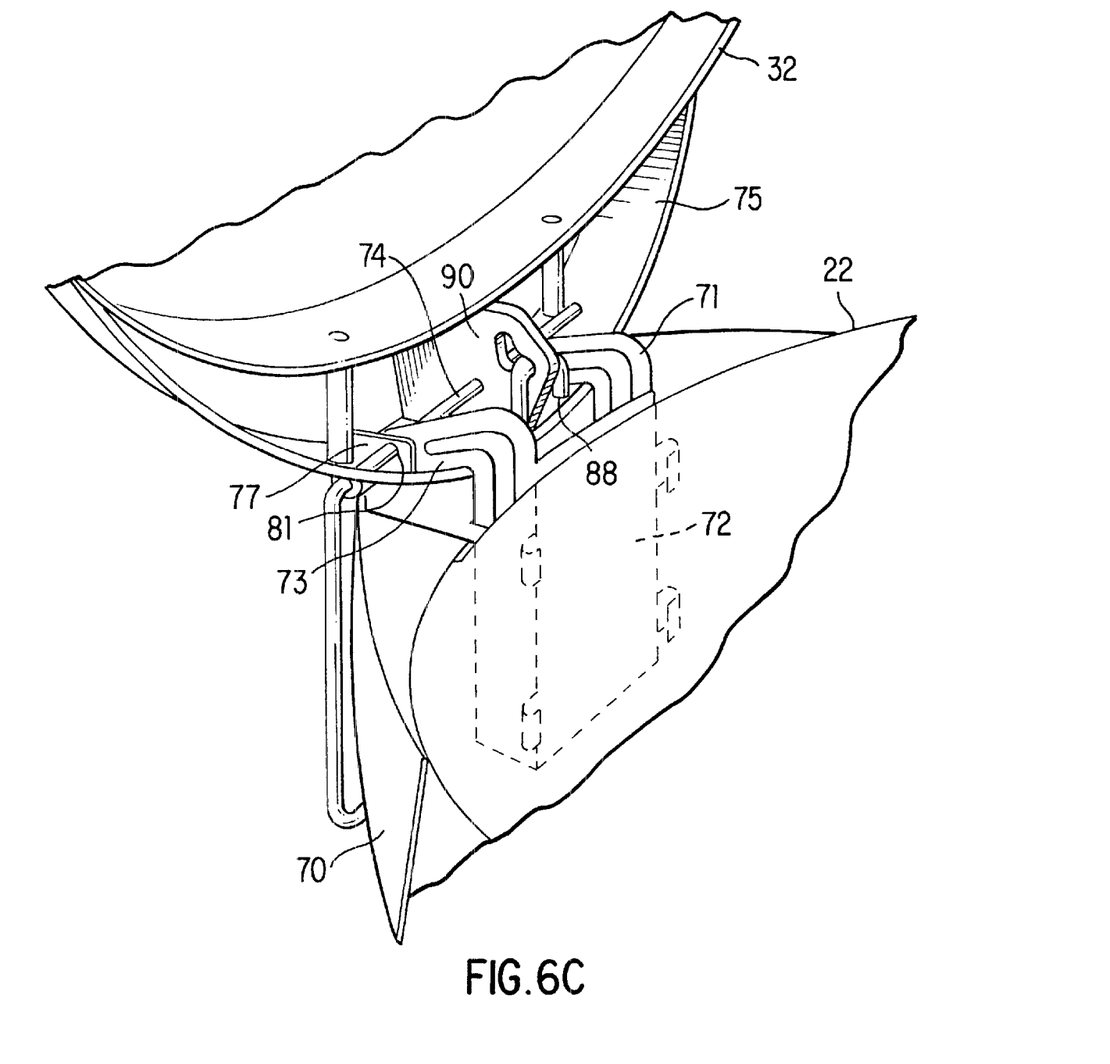
FIG. 6C illustrates the hinging portion between the lid and the shell of the trash can assembly of FIG. 1.
Figure 7:
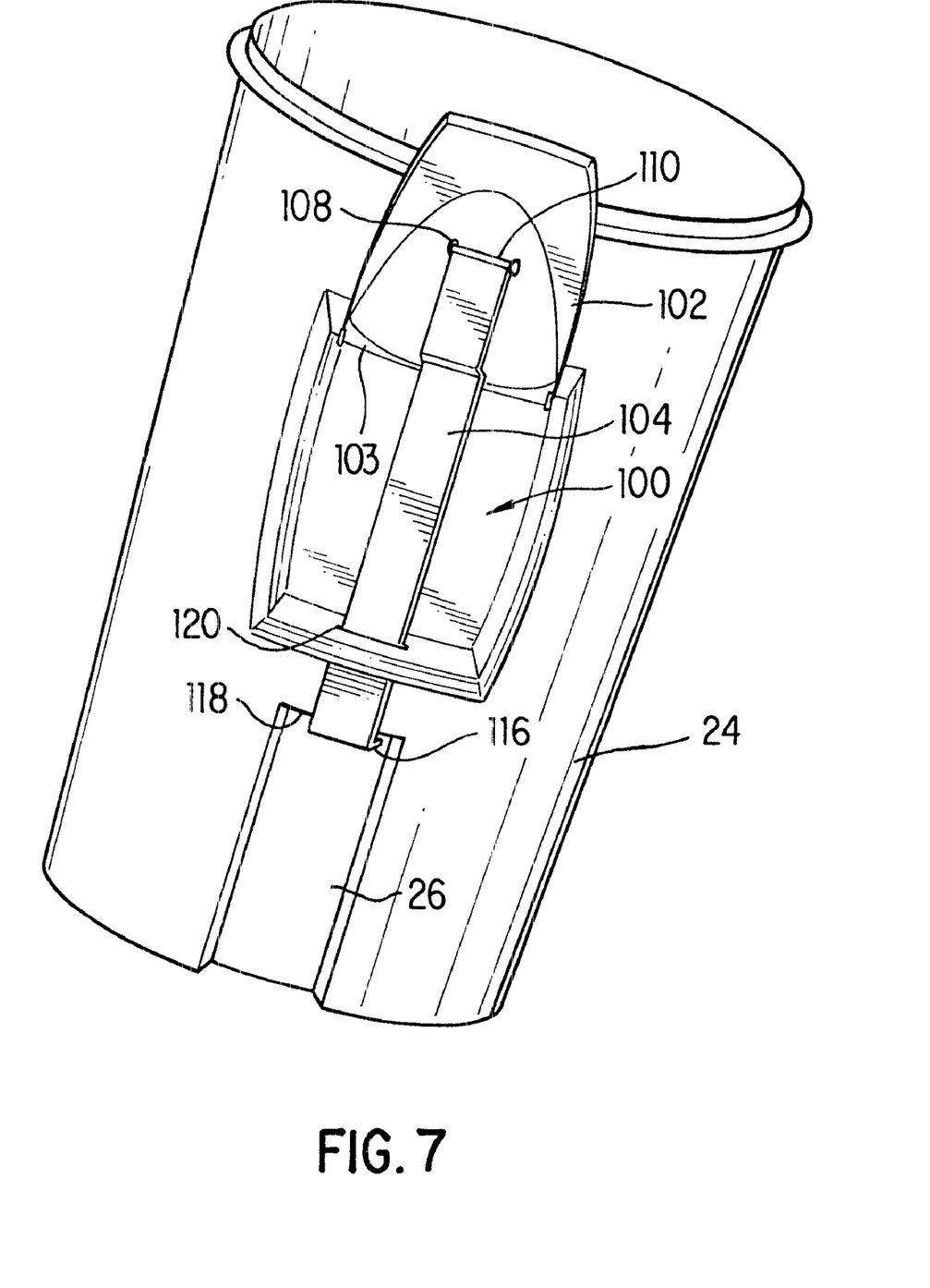
FIG. 7 illustrates how the handle mechanism of the trash can assembly of FIG. 1 operatively couples the liner of FIG. 4.

FIGS. 1–7 illustrate one embodiment of a trash can assembly 20 according to the present invention. The assembly 20 has an outer shell 22 and an inner liner 24 that is adapted to be retained inside the outer shell 22. As shown in FIGS. 3, 4 and 7, the liner 24 is a container that has an elongated indent 26 provided in the side wall 28 extending upwardly a short distance from the bottom 30 of the liner 24.

The outer shell 22 is a generally cylindrical shell that has a generally oval or egg shape. The liner 24 can have the same shape. The oval or egg shape of the shell 22 is best illustrated in the top plan view of FIG. 5. The width F of the opening at the front of the shell 22 is greater than the width R of the opening at the rear of the shell 22. This configuration for the shell 22 and its liner 24 allows the interiors of the shell 22 and the liner 24 to receive and accomodate wider and larger waste objects, such as pizza boxes. In addition, the narrower rear of the shell 22 allows the shell 22 to fit more easily in corners of the house.

A lid 32 is hingedly connected to the top of the outer shell 22. The shell 22 and its lid 32 can be made of a solid and stable material, such as a metal. A handle mechanism 34 is provided along the outer surface of the shell 22 and is operatively coupled to the indent 26 of the liner 24 for lifting the liner 24. A toe-kick recess 36 is provided on the shell 22 adjacent the base 38 of the shell 22, and is adapted to receive a foot pedal 40 that is pivotably secured to the base 38 of the shell 22. The toe-kick recess 36 is part of the base 38, and the shell 22 would define a curved cut-out to receive the recess 36. The curved cut-out in the shell 22 can be made by first cutting out a properly sized and configured hole in the body of the shell 22, and then inserting a plastic curved panel that defines the actual recess 36. The recess 36 extends upwardly for a short distance and extends into the interior confines of the shell 22. A link assembly 42 (illustrated in greater detail in FIGS. 6A and 6B) extends from the foot pedal 40 along the base 38 and then upwardly along the shell 22 to the lid 32. The link assembly 42 operates to translate an up-down pivot motion of the pedal 40 to an up-down pivot motion for the lid 32. Each of these components will be described in greater detail hereinbelow.

Referring first to FIGS. 2 and 3, the base 38 of the shell 22 defines a generally annular and curved skirt or flange portion 50. In one embodiment of the present invention, the skirt 50 is formed in one plastic piece. The base 38 further includes a pedal housing 52 that is positioned adjacent and below the recess 36, and is adapted to receive the pedal 40. In particular, a shaft 54 can extend longitudinally across the pedal 40 and be received inside openings provided on opposing walls 56 and 58 of the pedal housing 52. As a result, the pedal 40 would pivot about an axis defined by the shaft 54. The base 38 also has crossing support ribs 60 and 62 that are positioned adjacent the top of the skirt 50. The support ribs 60, 62 can be provided with protruding notches 68 that are adapted to hold and support a horizontal rod 64 of the link assembly 42 for rotation therein. In addition, pads 66, which can be made of rubber, can be positioned in spaced-apart manner about the periphery of the skirt 50 to prevent the base 38 from slipping. The shell 22 and its recess 36 can be attached to the top of the skirt 50 of the base 38 by glue, welding, screws, and similar attachment mechanisms.

Referring to FIG. 3, it will be noted that the foot pedal 40 is positioned somewhat inside the interior of the shell 22, and only a portion of the pedal 40 extends beyond the outer cylindrical periphery or surfaces of the shell 22. This positioning is of significance to the present invention.

One significance is that the foot pedal 40 can extend radially outwardly from the shell 22 by about the same extent as the skirt 50, and is configured so that the foot pedal 40 itself appears to form part of the skirt 50 (i.e., flush with the skirt 50) to provide a more aesthetically pleasing appearance. This positioning makes the foot pedal 40 less susceptible to being inadvertently kicked by people walking around the vicinity of the trash can assembly 20. More importantly, by positioning most of the step pedal 40 inside the outer periphery of the shell 22, a larger pedal 40 (i.e., a pedal 40 with a larger top or stepping surface area) can be provided to create additional stepping space. This increased stepping space makes it easier for the user to step on the pedal 40, and to maintain the step, because this increased stepping space helps to generate more power during the step (for the reasons explained in the next paragraph).

Another significance is shown in FIG. 3, where the pivot point (i.e., shaft 54) of the foot pedal 40 is positioned well inside the interior of the outer periphery of the shell 22. This is to be contrasted with conventional foot pedals, whose pivot points are usually positioned further outwardly, and usually outside the shell 22, such as illustrated in U.S. Pat. No. 6,010,024. This inward position for the pivot point provides several benefits. First, this inward position for the pivot point provides a smaller pivoting angle for the pedal 40. The smaller pivoting angle means that the user's foot does not need to pivot as much to effectively step on the pedal 40, so that the user's foot is less likely to slip when stepping on the pedal 40. Second, this inward position for the pivot point requires less stepping force to open the lid 32 (i.e., deploy the link assembly 42) than if the pivot point were positioned further radially outwardly. This is because providing the pivot point further inside the outer periphery of the shell 22 allows the pedal 40 to be provided in a larger size, as discussed in the previous paragraph. Having a larger size allows the distance from the pivot point to the outer edge of the pedal 40 to be increased, and this increased distance means that more power can be generated using less force.

Yet another significance is that since the foot pedal 40 is constructed as part of the base 38, the pedal 40 can be positioned closer to the ground (i.e., vertically lower). As a result, the user's foot does not need to pivot as much to effectively step on the pedal 40, so that the user's foot is less likely to slip when stepping on the pedal 40.

FIGS. 3, 6A and 6C illustrate how the lid 32 is hingedly coupled to the shell 22. A hinge housing 70 is provided adjacent the top of the shell 22. A carrying handle 130 can be provided on the outer surface of the hinge housing 70. A hinge bracket 72 is attached at the top of the hinge housing 70, and carries two spaced-apart L-shaped extensions 71 and 73. The rear of the lid 32 has a plastic hinge piece 75 that carries two spaced-apart plates 77 (one of the plates adjacent extension 71 is not visible in FIG. 6C). An opening 81 is provided in each extension 71, 73 and plates 77, the openings 81 being aligned so that a pin 74 (which can be part of the carrying handle 130) can extend through all the openings 81 in the extensions 71, 73 and the plates 77 to create a pivot joint. Thus, the lid 32 is able to pivot from the opened position (see FIG. 3) to the closed positioned (see FIG. 2) about the pivot point defined by the pin 74.

Referring now to FIGS. 2, 3, 6A and 6B, the link assembly 42 operatively couples the foot pedal 40 to the lid 32 so that stepping on the foot pedal 40 will cause the lid 32 to open. The link assembly 42 has a horizontal rod 64 and a vertical rod 76 that cooperate to translate an up-down pivot motion of the pedal 40 to an up-down pivot motion for the lid 32. The rods 64 and 76 can be made of steel. In particular, the horizontal rod 64 is held by the ribs 60, 62 of the base 38, and has an L-shaped (i.e., at 90-degrees) terminal end 78 that extends out of the horizontal plane of the rod 64, and which is positioned adjacent the bottom of the pedal 40. For example, the terminal end 78 does not need to be connected to pedal 40, since the pedal 40 can can sit on top of the terminal end 78 via gravity. The horizontal rod 64 extends across the base 38 to an opposite side of the shell 22, where an opposing end 80 of the horizontal rod 64 has an L-shaped leg 82 (i.e., at 90-degrees) that also extends out of the horizontal plane of the rod 64, and that is secured to a generally L-shaped (i.e., 90-degree) plastic hinge 84. The plastic hinge 84 can have two lumens, one in each leg of the L-shape, with the leg 82 secured in one of the lumens and a lower end 86 of the vertical rod 76 secured in the other lumen. The vertical rod 76 extends vertically up along the inside of the shell 22 adjacent the inner wall of the shell 22, and extends through the hinge housing 70 and the hinge bracket 72 to an upper end 88 that is secured to a block 90 that is attached to the rear of the lid 32 and retained in the hinge piece 75. Thus, when the user steps on the pedal 40 (see arrow A1 in FIG. 3 and arrow A1 in FIG. 6A), the pedal 40 presses on the terminal end 78, and the L-shaped and out-of-plane nature of the terminal end 78 causes the horizontal rod 64 to rotate as shown by the arrow A2. Because the opposing end 80 is also L-shaped and extends out of the horizontal plane of the rod 64, this rotation torques the plastic hinge 84 to push the vertical rod 76 up (see arrow A3). When the vertical rod 76 is pushed up, the vertical rod 76 will in turn push the lid 32 upwardly to pivot or swing the lid 32 open about the pin 74. As long as the user's foot is stepping on the pedal 40, the link assembly 42 will maintain the lid 32 in its opened position. When the user releases the stepping force, gravity will push the lid 32 and vertical rod 76 down, pivoting or torquing the plastic hinge 84 in a direction opposite to the direction of arrow A3, and reversing the rotation on the horizontal rod 64 to lift up the pedal 40 in directions opposite to the directions of arrows A1 and A2.

Referring now to FIGS. 1, 3 and 7, the handle mechanism 34 operates to lift the liner 24 from the interior of the shell 22, and can be locked to maintain the liner 24 in the lifted position shown in FIGS. 1 and 3. The shell 22 has a recessed region 100 provided about its central portion. The recessed region 100 has a generally square or rectangular configuration, and is adapted to receive the handle 102 and link strip 104 of the handle mechanism 34. The handle mechanism 34 has a handle 102 that is pivotably coupled to a link strip 104. The handle 102 can be a generally flat piece of plastic or metal, and can be pivotably coupled adjacent its lower side 103 to the shell 22 at the top of the recessed region 100 (e.g., by inserting a pin 105 through a bore adjacent the lower side 103). The link strip 104 is preferably made from a material with sufficient strength to support the liner 24, such as plastic, steel, or a composite of plastic and steel. The link strip 104 has a first section 106 that is pivotably coupled (e.g., by inserting a pin 108 through a bore 110 at the end of the first section 106) to a mid-portion of the handle 102. The link strip 102 has a second section 112 that extends perpendicularly to and inwardly from the first section 106, which is then connected to an elongated third section 114 that is generally parallel to the first section 106. The third section 114 extends through a slot 120 in the recessed region 100 to extend inside the shell 22. The third section 114 has a hooked end 116 that is always positioned inside the shell 22, and which is adapted to engage the upper wall 118 of the indent 26. FIG. 7 illustrates the liner 24, and only the recessed region 100, handle 102 and link strip 104 while omitting the other elements of the shell 22.

FIGS. 1, 3 and 7 illustrate the handle 102 in the lifted or removal position, with the liner 24 being lifted partially out of the interior of the shell 22. To close the handle 102 and allow the liner 24 to fall back into the shell 22, the handle 102 is pivoted downwardly in the direction of the arrow A4. The pivoting of the handle 102 occurs about the pivot axis defined by the pin 105. The pivoting of the handle 102 simultaneously causes the link strip 104 to pivot about the handle 102 about the pivot axis defined by the pin 108. As the link strip 104 pivots, it is pushed vertically downwardly by the handle 102. As the link strip 104 slides down, the hooked end 116 also slides down within the elongated indent 26. The force of gravity will cause the liner 24 to slide down the interior of the shell 22 together with the hooked end 116. After the handle 102 has been pivoted by 180 degrees from the position shown in FIGS. 1, 3 and 7, the handle 102 will be in the storage or lowered position and will occupy most of the recessed region 100.

To lift the liner 24 from the storage position to the lifted or removal position, the handle 102 is pivoted upwardly in the direction opposite to the direction of the arrow A4. The upwardly pivoting handle 102 will actuate the pivots about the pins 105 and 108, which will cause the link strip 104 to be pulled upwardly. As the link strip 104 moves upwardly, its hooked end 116 (which is in engagement with the upper wall 118 of the indent 26) will simultaneously pull the liner 24 upwardly within the shell 22. Once the handle 102 is pivoted upwardly to about 120 degrees (i.e., also referred to as an "over-center" position) from its vertical storage position, the handle 102 will reach a locked position so that the handle 102 will be automatically biased to the vertical lifted or removal position shown in FIGS. 1, 3 and 7. When the handle 102 reaches this lifted or removal position, the liner 24 will be lifted to the position shown in FIGS. 1 and 3 (i.e., a portion of the liner 24 being lifted out of the shell 22), and will be maintained in this position by the locked handle 102 until the handle 102 is pivoted downwardly again in the direction of the arrow A4.

Figure 8:
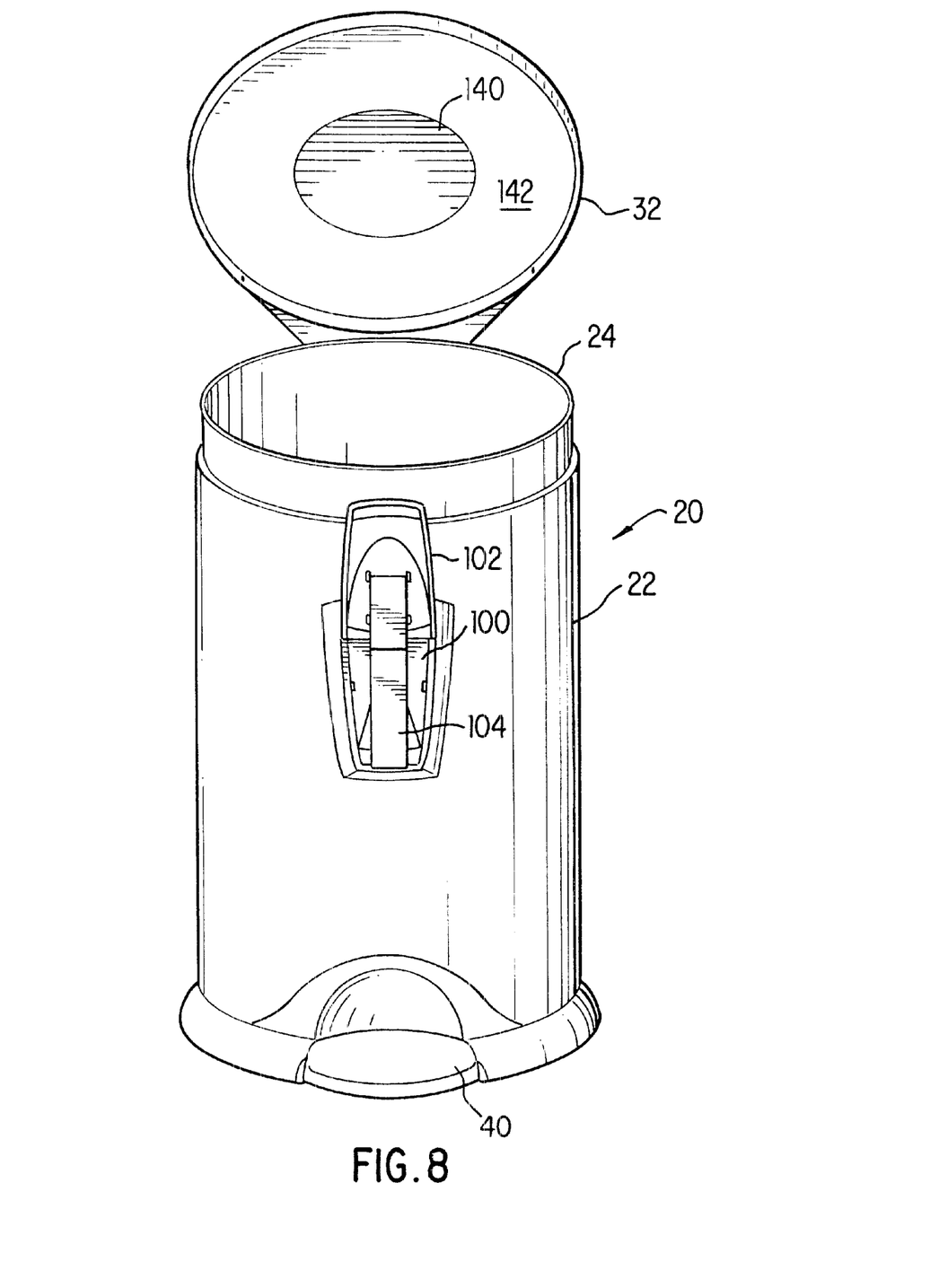
FIG. 8 is a front plan view of the trash can assembly of FIG. 1.

The present invention also provides apparatus to combat the foul odor of the waste products stored inside the trash can assembly 20. FIGS. 3 and 8 illustrate one embodiment, where a charcoal pad 140 can be secured to the inner surface 142 of the lid 32 by a removable attachment mechanism 132, which can be a nipple connector, opposing VELCRO™ pads, a hook, a fastener, glue, a screw-in connection, or the like. The charcoal pad 140 can be any conventional charcoal pad, which is activated carbon that functions to absorb odor. The air flow (see arrows in FIG. 3 that are directed towards charcoal pad 140) enhances the absorption of odor by forcing air through the charcoal, causing the charcoal to absorb the odor carried by the air.

Figure 9:
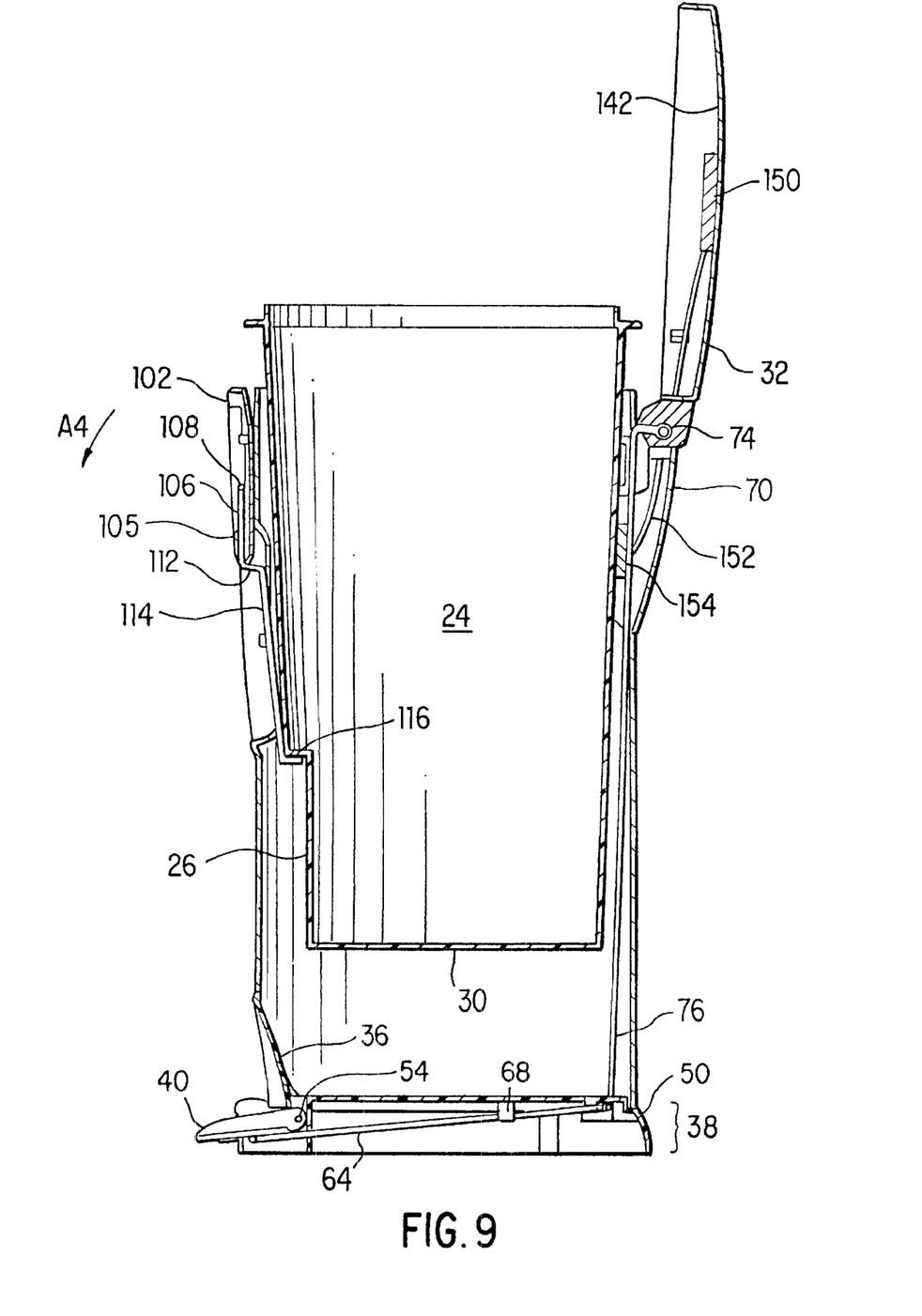
FIG. 9 is a cross-sectional side view of a trash can assembly according to another embodiment of the present invention, illustrating a modification to the trash can assembly of FIGS. 1–8.
Figure 10:
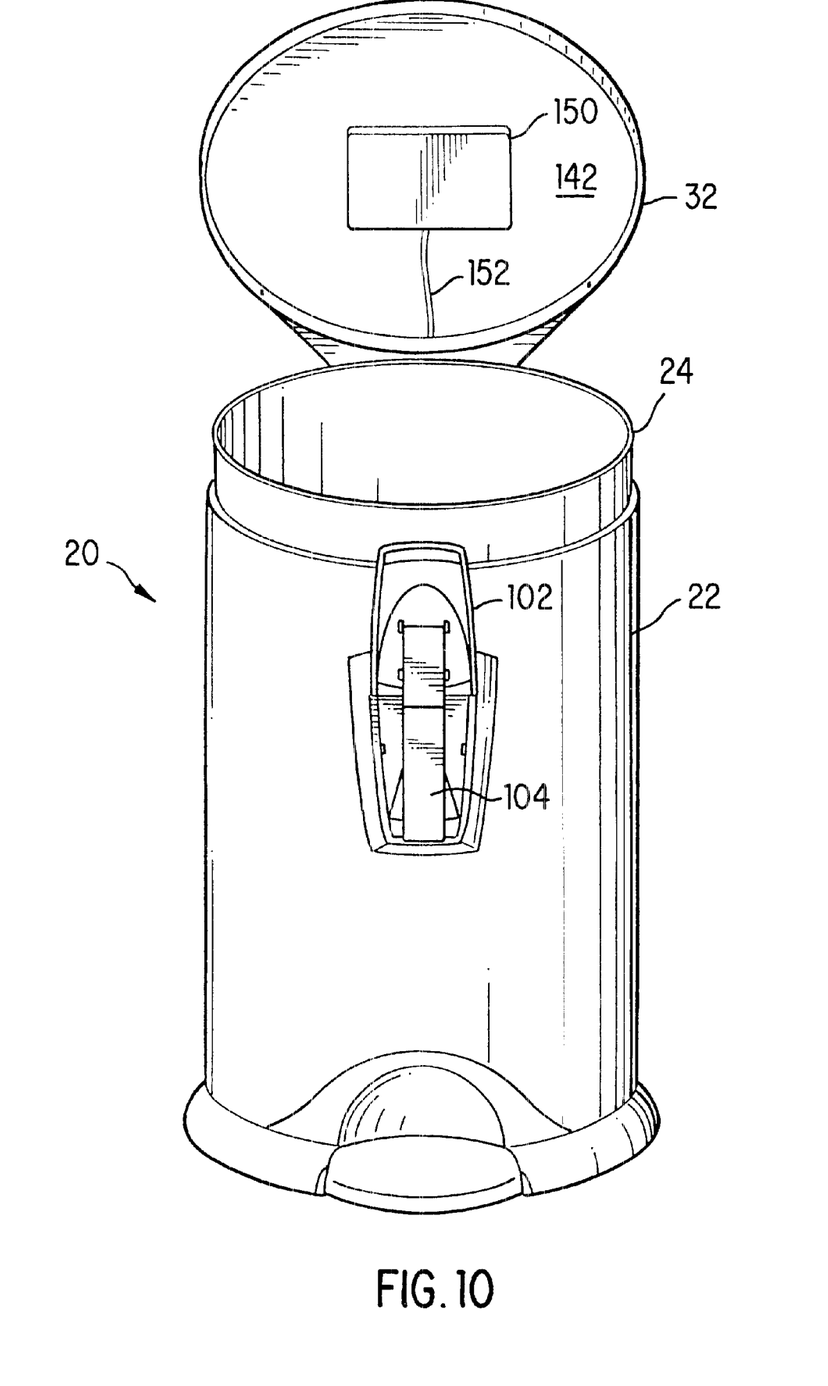
FIG. 10 is a front plan view of the trash can assembly of FIG. 9.

FIGS. 9 and 10 illustrate another embodiment, where an ionizer box 150 can be secured to the inner surface 142 of the lid 32 by any of the attachment mechanisms 132 described above. Alternatively, the ionizer box 150 can be formed as part of the lid 32, and provided with an opening through which electric ions can be introduced and removed. A power cord 152 couples the ionizer box 150 and extends from the ionizer box 150 into the interior of the hinge housing 70 and coupled to a power source 154, which can be a battery pack. The power source 154 can be secured to the shell 22. By locating the power source 154 in the hinge housing 70, the present invention avoids adding unnecessary weight to the lid 32, making it easier for the user to open the lid 32, and to keep the lid 32 opened. The ionizer functions by forcing $O_2$ (oxygen) into $O_3$ (via electric charge), with the third oxygen molecule splitting off with the pollutant, leav ing behind fresh $O_2$ (oxygen). The ionizer can be turned on at all times, or a sensor (not shown) can be incorporated to sense the opening and closing of the lid 32 (i.e., sense movement). As a result, the sensor will sense movement of the lid 32 and then function to turn on the ionizer for a specified time (e.g., fifteen minutes).

Thus, the trash can assembly 20 of the present invention provides an improved and larger pedal 40 that is positioned and structured to provide more effective opening of the lid 32 and more convenient use by the user. In addition, the handle mechanism 34 provides an effective mechanism for lifting the liner 24 out of the shell 22, and for maintaining the liner 24 in the lifted position. Moreover, apparatus can be provided on the lid 32 to combat foul odor.

The above detailed description is for the best presently contemplated modes of carrying out the invention. This description is not to be taken in a limiting sense, but is made merely for the purpose of illustrating general principles of embodiments of the invention. The scope of the invention is best defined by the appended claims. In certain instances, detailed descriptions of well-known devices, components, mechanisms and methods are omitted so as to not obscure the description of the present invention with unnecessary detail.

What is claimed is:

1. A trash can assembly, comprising:
   a shell having a top end and a bottom end, the shell having a metal enclosing wall that defines a periphery, the enclosing wall having a recess at its bottom end;
   a curved recess panel, separate from the shell, that is fitted in the recess, the curved recess panel made of a non-metal material;
   a lid fitted over the top end;
   a foot pedal partially positioned in the recess panel, with a portion of the foot pedal positioned inside the periphery of the shell; and
   a link assembly coupling the foot pedal and the lid.

2. The assembly of claim 1, wherein the foot pedal has a top surface area, and wherein a portion of the top surface area of the foot pedal is positioned inside the periphery of the shell.

3. The assembly of claim 1, wherein the foot pedal pivots about a pivot point, with the pivot point positioned inside the periphery of the shell.

4. The assembly of claim 1, further including a base, with the foot pedal pivotally secured to the base.

5. The assembly of claim 1, wherein the shell has an oval configuration, with a front width that is longer than a rear width.

6. The assembly of claim 1, further including:
   a liner defining a container body, the liner fitted inside the shell and having an indent provided on the container body; and
   a handle mechanism having a link strip that has a hooked end, the hooked end engaging the indent to lift the liner from inside the shell.

7. The assembly of claim 1, wherein the enclosing wall of the shell is made of metal, and the recess panel is made of plastic.

8. A trash can assembly, comprising:
   a shell having an enclosing wall that defines a periphery;
   a liner defining a container body that has a side wall, the liner fitted inside the shell and having an indent provided on the side wall of the container body; and
   a handle mechanism having a link strip that has a hooked end, the hooked end engaging the indent to lift the liner from inside the shell;
   wherein the link strip is positioned adjacent the enclosing wall of the shell and the side wall of the container body.

9. The assembly of claim 8, wherein the shell has a top end and a bottom end, the assembly further including:
   a lid fitted over the top end;
   a foot pedal positioned adjacent the bottom end, with a portion of the foot pedal positioned inside the periphery of the shell; and
   a link assembly coupling the foot pedal and the lid.

10. A trash can assembly, comprising:
    a shell having an enclosing wall that defines a periphery;
    a liner defining a container body, the liner fitted inside the shell and having an indent provided on the container body; and
    a handle mechanism having a link strip that has a hooked end, the hooked end engaging the indent to lift the liner from inside the shell;
    wherein a first part of the link strip extends outside the enclosing wall of the shell, and a second part of the link extends inside the enclosing wall of the shell, and wherein the hooked end is coupled to the second part; and
    wherein the handle mechanism further includes a handle piece that is pivotally coupled to the enclosing wall of the shell and the first part of the link strip.

11. The assembly of claim 10, wherein the handle piece locks the link strip in a fixed position when the handle piece is pivoted pass an over-center position.

12. The assembly of claim 10, wherein the enclosing wall of the shell has a recessed region which receives the handle piece and the link strip.

13. The assembly of claim 10, wherein the link strip slides downwardly when the handle piece is pivoted downwardly.

14. The assembly of claim 10, wherein the link strip slides upwardly when the handle piece is pivoted upwardly.

15. A trash can assembly, comprising:
    a shell having a top end and a bottom end, the shell having an enclosing wall that defines a periphery;
    a curved recess panel that is fitted in the enclosing wall adjacent the bottom end of the shell, the curved recess panel made of a different material than the enclosing wall of the shell;
    a lid fitted over the top end;
    a foot pedal partially positioned in the recess panel, with a portion of the foot pedal positioned inside the periphery of the shell;
    a link assembly coupling the foot pedal and the lid; and
    a plastic base that is separate from the enclosing wall, with the foot pedal pivotally secured to the base, and wherein the enclosing wall is made of metal.

* * * * *